US00PP32430P2

(12) United States Plant Patent
Olesen

(10) Patent No.: US PP32,430 P2
(45) Date of Patent: Nov. 10, 2020

(54) HYBRID TEA ROSE PLANT NAMED 'POULREN032'

(50) Latin Name: ***Rosa* hybrid**
Varietal Denomination: Poulren032

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,244

(22) Filed: Sep. 4, 2019

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./101, 130, 137
See application file for complete search history.

*Primary Examiner* — Susan McCormick Ewoldt

(57) ABSTRACT

A new garden rose plant of the Hybrid Tea class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulren032'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulren032', originated as a single seedling from the stated cross.

The new variety may be distinguished from its male pollen parent and female seed parent primarily by the following characteristics. The male pollen parent plant has a growth height of 65 cm while the new variety has a growth height of 100 cm. The female seed parent plant has red flowers while the new variety has pink flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance; and
4. Perfumed flowers.

This combination of qualities is not present in previously available commercial cultivars of this type, known to the inventor, and distinguish 'Poulren032' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulren032' was selected in the spring of 2013 by the inventor as a single plant from the progeny of the aforementioned hybridization.

Asexual reproduction of 'Poulren032' by rooted cuttings was first done by Mogens N. Olesen in the nursery in Fredensborg, Denmark in July, 2013. This initial and other subsequent asexual propagations conducted in controlled environments have demonstrated that the characteristics of 'Poulren032' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren032'.

Specifically illustrated in FIG. 1 of the drawings are open flowers viewed from above and the side, petals detached, and sepals detached revealing reproductive flower parts.

Figure 1:
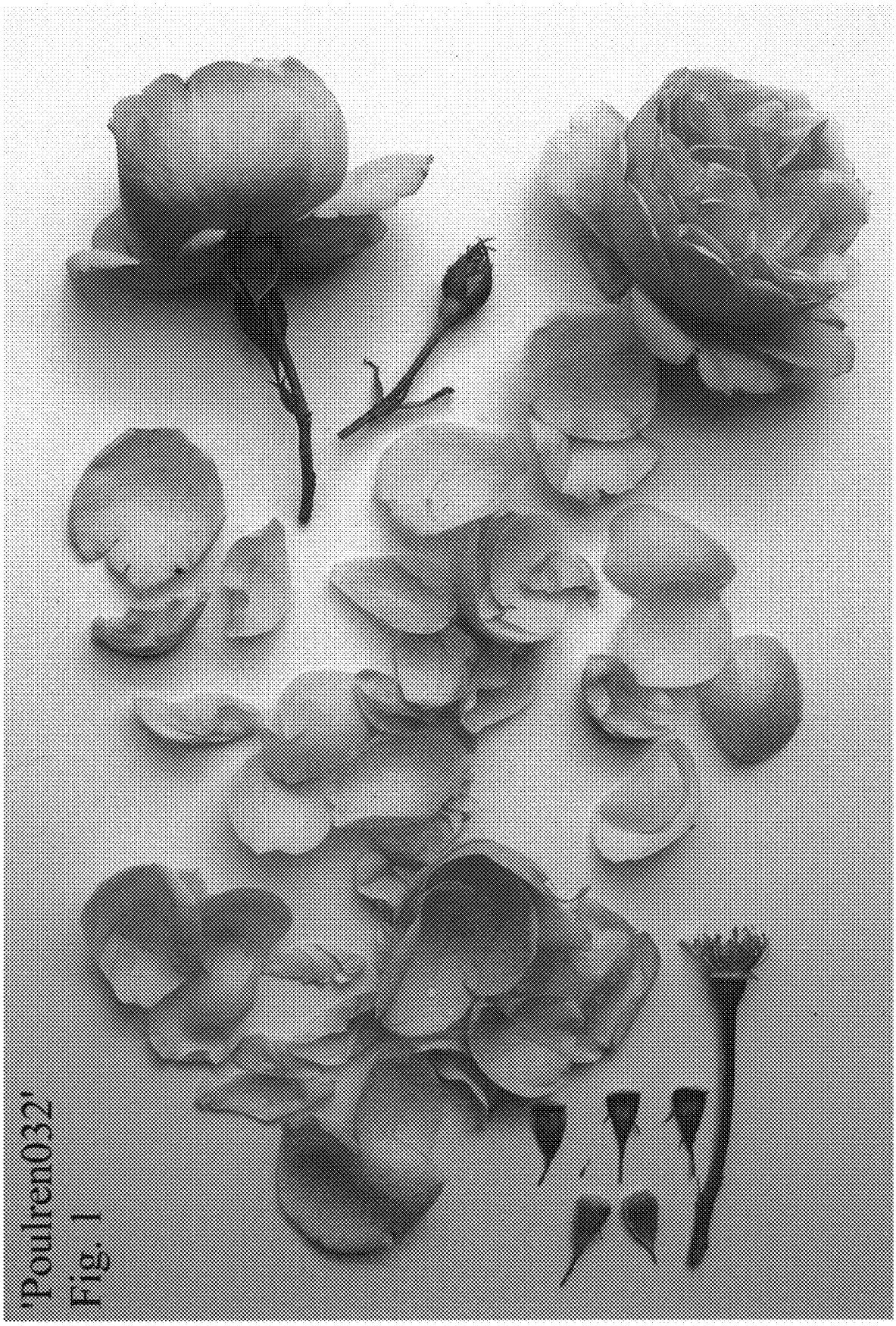
Figure 2:
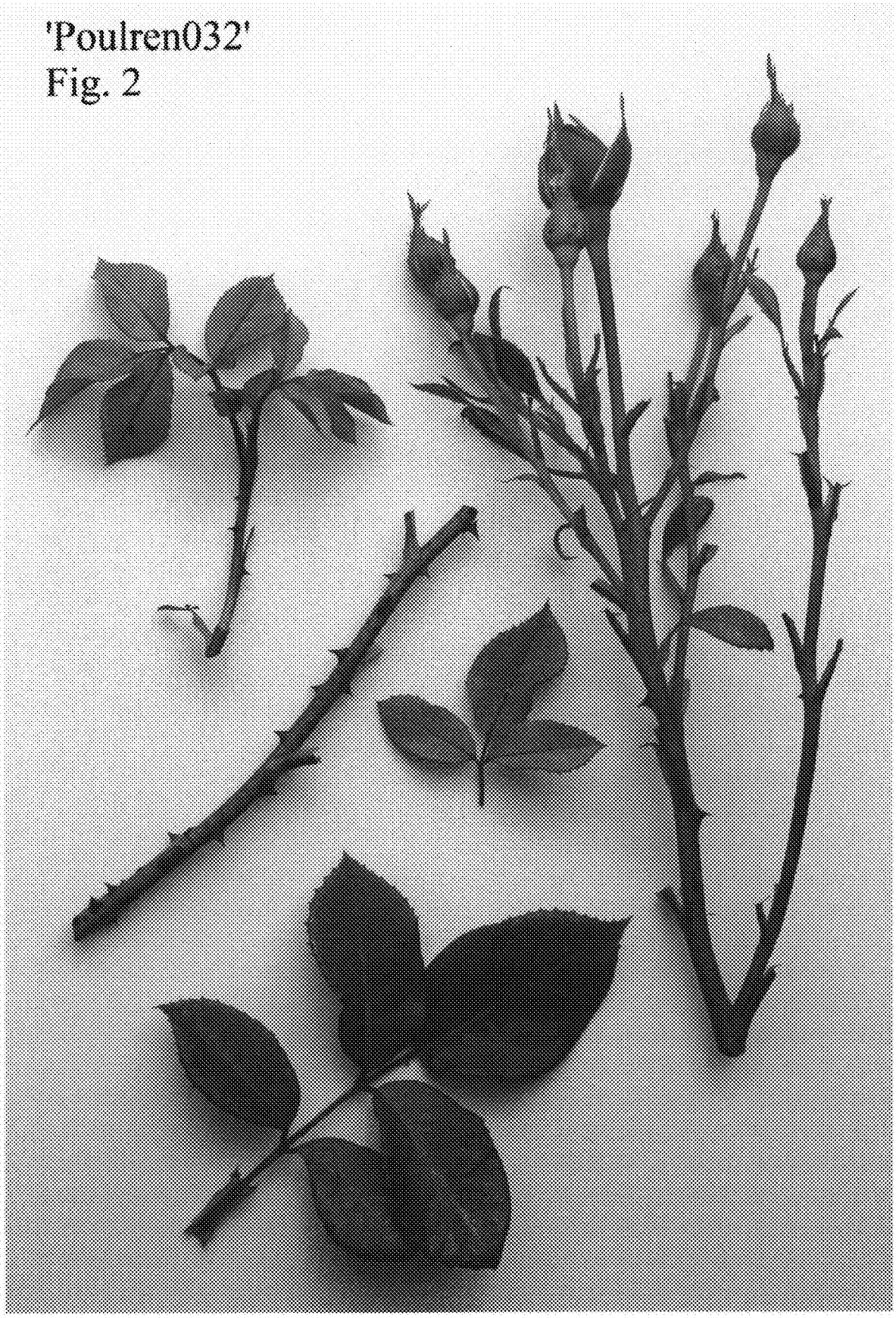

Specifically illustrated in FIG. 2 of the drawings are juvenile and mature leaves, bare stem, and a flowering branch showing flower buds. Plants shown are 2 years of age.

DETAILED DESCRIPTION OF THE VARIETY

The following is a description of 'Poulren032', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren013', U.S. Plant Pat. No. 16,541 are compared to 'Poulren032' in Chart 1.

CHART 1

| | 'Poulren032' | 'Poulren013' |
|---|---|---|
| Petal Count | 100 petals | 50 petals |
| Flower Diameter | 80 mm | 85 mm |

CHART 1-continued

| | 'Poulren032' | 'Poulren013' |
|---|---|---|
| General Tonality of Flower Color | Red Group 49A. | Red-Purple Group 61D |

FLOWER AND FLOWER BUD

Blooming habit: Continuous.

Flower bud:

*Size.*—Upon opening, 26 mm in length from base of receptacle to end of bud. Bud diameter is 14 mm.

*Bud form.*—Broad based ovoid.

*Bud color.*—As sepals divide petals are Red Group 38A.

*Sepal inner surface.*—Color: Yellow-Green Group 145B with intonations of Greyed-Orange Group 177B. Surface: Lightly pubescent.

*Sepal outer surface.*—Color: Yellow-Green Group 144A with intonations of Greyed-Red Group 180A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—32 mm long, 10 mm wide.

*Receptacle.*—Texture: Smooth. Size: 8 mm in height, 9 mm wide. Color: Yellow-Green Group 144A with intonations of Greyed-Red Group 180B. Shape: Campanulate.

*Pedicel.*—Surface: Smooth. Length: 33 mm. Diameter: 2 mm on average. Color: Yellow-Green Group 151A with intonations of Greyed-Red Group 180A. Strength: Strong.

*Peduncle.*—Length: 3 to 15 cm. Diameter: About mm. Color: Yellow-Green Group N144A. Texture: Smooth.

Flower bud development: Flower buds are borne singly and in clusters of about 7 flower buds per stem.

Flower bloom:

*Fragrance.*—Strong perfume.

*Duration.*—The blooms have a duration on the plant of approximately 10 days. Petals fall cleanly away from plant after flowers have fully matured.

*Size.*—Flower diameter is 80 mm when open. Flower depth is 45 mm.

*Flower shape.*—Quartered-rosette, very double, with many overlapping petals packed into quarter sections.

*Shape of flower, side view.*—The upper portion is flat. The lower portion is flattened concave.

Petalage: Under normal conditions, flowers have about 100 petals.

General tonality of flower: Open flowers are Red Group 49A.

Petal color:

*Upon opening, outer petals.*—Upper surface: Red Group 56A. Lower surface: Red-Purple Group 73D splashed with Red-Purple Group 73B.

*Upon opening, inner petals.*—Upper surface: Red Group 56A splashed with Red- Purple Group 56C. Lower surface: Red-Purple Group 73D splashed with Red-Purple Group 73B.

*Basal petal spots, upon opening.*—Upper surface: Green-White Group 157A. Lower surface: Green-White Group 157A.

*After opening, outer and inner petals.*—Upper surface: Red Group 56A. Lower surface: Red-Purple Group N57C.

*Basal petal spots, after opening.*—Upper surface: Green-White Group 157A. Lower surface: Green-White Group 157A.

Petals:

*Petal reflex.*—Slightly reflexed.

*Margin.*—Entire and uniform. Weak undulations.

*Shape.*—Broad and elliptic. Apex shape: Rounded. Base shape: Acute.

*Size.*—50 mm (l)×50 mm (w).

*Texture.*—Smooth.

*Thickness.*—Average.

Petaloids:

*Size.*—20 mm (l) by 14 mm (w).

*Quantity.*—About 10.

*Shape.*—Elliptical with an acute base and rounded apices.

*Color.*—The upper surface of petaloids is Red Group 56A splashed with Red-Purple Group 56C. The lower surface is Red-Purple Group 73D splashed with Red-Purple Group 73B. At the base, Green-White Group 157A.

Reproductive flower parts:

*Pollen.*—None observed.

*Anthers.*—Size: 3 mm in length. Color: Greyed-Orange Group 163C. Quantity: 48 on average.

*Filaments.*—Color: Greyed-Red Group 180C. Length: 5 mm.

*Pistils.*—Length: 4 mm. Quantity: 35 on average.

*Stigmas.*—Color: Greyed-Yellow Group 160B.

*Styles.*—Color: Greyed-Yellow Group 160B.

*Location of stigmas.*—Inferior in location relative to the length of the filaments and the height of the anthers.

*Hips.*—None Observed.

PLANT

Plant growth: Upright, bushy. Plants are about 100 cm in height, and 85 cm wide.

Stems:

*Color of juvenile growth.*—Yellow-Green Group 144B.

*Color of mature growth.*—Yellow-Green Group 144A.

*Length.*—Canes are about 50 cm from the base of the plant to the flowering portion.

*Diameter.*—About 5 to 6 mm.

*Internodes.*—On mature canes about 35 mm between nodes.

*Surface texture.*—Young wood: Smooth. Older wood: Rough.

Long prickles:

*Incidence.*—12 prickles per 10 cm of stem.

*Size.*—Average length of prickles on mature stems is 7 mm.

*Shape.*—Upper portion is linear. Lower portion is concave.

*Color.*—Juvenile prickles: Greyed-Red Group 180B. Mature prickles: Greyed-Red Group 180B.

Plant foliage:

*Compound leaf.*—125 mm (l)×110 mm (w).

*Quantity.*—2 leaves per 10 cm of stem on average.

*Leaf bearing angle to the stem.*—45 degrees.

*Color of juvenile foliage.*—Upper side: Yellow-Green Group N144A with marginal intonations of Greyed-Red Group 178B. Lower side: Yellow-Green Group N144A with marginal intonations of Greyed-Red Group 178B.

*Color of mature foliage.*—Upper side: Yellow-Green Group 147A. Lower side: Yellow-Green Group 147B.

Plant leaves and leaflets:

*Stipules.*—Size: 15 mm long, 4 mm wide. Quantity: 2 per compound leaf. Shape: Linear, slightly broad based with outward extending apices. Margins: Finely serrated. Color: Yellow-Green Group N144A.

*Petiole.*—Length: 20 mm. Diameter: 3 mm. Upper surface color: Greyed-Orange Group 173A. Lower surface color: Yellow-Green Group 144A.

*Rachis.*—Length: 50 mm Upper surface color: Greyed-Orange Group 173A. Lower surface color: Yellow-Green Group 144A.

*Leaflet.*—Quantity: Normally 5 leaflets. Margins: Serrated. Size: Terminal leaflets are about 50 mm long, 32 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Hybrid Tea rose class named 'Poulren032', substantially as illustrated and described herein, due to its abundant pink flowers, disease resistance, and extended period of bloom.

* * * * *

'Poulren032'

'Poulren032'